United States Patent [19]

Kobayashi et al.

[11] Patent Number: 4,937,047
[45] Date of Patent: Jun. 26, 1990

[54] ANALYTICAL ELEMENT

[75] Inventors: Morio Kobayashi; Seiji Hidaka; Takashi Ishihara; Isao Haga; Hiroshi Iwadate, all of Hino, Japan

[73] Assignee: Konishiroku Photo Industry Co., Ltd., Tokyo, Japan

[21] Appl. No.: 31,698

[22] Filed: Mar. 27, 1987

[30] Foreign Application Priority Data

Apr. 1, 1986 [JP] Japan .................................. 61-75997
Sep. 19, 1986 [JP] Japan ................................ 61-219175

[51] Int. Cl.$^5$ ..................... G01N 33/48; G01N 31/22; G01N 33/50
[52] U.S. Cl. .......................................... 422/56; 422/58; 435/16; 435/17; 435/25; 435/805; 435/436; 436/71; 436/169
[58] Field of Search ...................... 422/56, 58; 436/71, 436/171, 169; 435/11, 16, 17, 22, 25, 24, 805

[56] References Cited

U.S. PATENT DOCUMENTS

| | | | |
|---|---|---|---|
| Re. 30,267 | 5/1980 | Bruschi ................... | 422/56 |
| 3,956,069 | 5/1976 | Allain et al. .............. | 435/14 |
| 3,992,158 | 11/1976 | Przybylowicz et al. .... | 435/11 |
| 4,144,306 | 3/1979 | Figueras .................. | 422/56 |
| 4,153,668 | 5/1979 | Hill et al. ................ | 422/56 |
| 4,322,496 | 3/1982 | Esders .................... | 435/25 |
| 4,390,343 | 6/1983 | Walter .................... | 422/57 |
| 4,391,906 | 7/1983 | Bauer ..................... | 422/57 |
| 4,557,901 | 12/1985 | Koyama et al. ........... | 435/805 |

FOREIGN PATENT DOCUMENTS

| | | |
|---|---|---|
| 0140589 | 5/1985 | European Pat. Off. . |
| 0149853 | 7/1985 | European Pat. Off. . |
| 0200541 | 11/1986 | European Pat. Off. . |
| 2269080 | 11/1975 | France . |
| 2026692 | 2/1980 | United Kingdom . |

Primary Examiner—Barry S. Richman
Assistant Examiner—Lyle Alfandary Alexander
Attorney, Agent, or Firm—Frishauf, Holtz, Goodman & Woodward

[57] ABSTRACT

An analytical element for analyzing a specific component in a liquid sample, comprising a light-transmissive and liquid-impermeable support having thereon successively a first reagent layer and a second reagent layer, and a porous spreading layer provided above said second reagent layer, and containing an electron transport agent, a dye-forming precursor material, an oxidized type coenzyme, a buffering agent and at least one reagent capable of converting said oxidized type coenzyme to a reduced type coenzyme through a specific component in a liquid sample, wherein said oxidized type coenzyme is contained in said porous spreading layer, and a lactate dehydrogenase inhibitor is contained in at least one of said second reagent layer and said porous spreading layer.

According to this invention, error originating from LDH and lactic acid present in a biological liquid sample can be eliminated and the accuracy of analysis can be improved.

18 Claims, No Drawings

ANALYTICAL ELEMENT

BACKGROUND OF THE INVENTION

This invention relates to an analytical element, particularly, to an analytical element for analyzing specific components in a liquid sample, and, more particularly, to a dry analytical element for analyzing specific components in a biological liquid sample through a reduced type coenzyme.

Analytical elements of various constitution have been known about dry analytical elements for analyzing specific components in a biological liquid sample. Among them, an analytical element utilizing a reaction system in which a dye is formed by transferring a reduced type coenzyme produced under the participation of a dehydrogenase and an oxidized type coenzyme to a dye-forming precursor material through means of an electron transport agent, is disclosed in detail, for example, in Japanese Unexamined Patent Publications No. 88097/1984 and No. 91896/1984, and Japanese Unexamined Patent Publication No. 262660/1986.

However, except for the analysis of lactate dehydrogenase and the analysis of a specific component by utilizing an oxidized type nicotinamide adenine dinucleotide phosphate (NADP+) as an oxidized type coenzyme, the analytical element disclosed in these publications may suffer an error due to the nonspecific reduction of lactate dehydrogenase (LDH) and an oxidized type nicotinamide adenine dinucleotide (NAD+) originating from lactic acid present in a biological liquid sample, whereby the accuracy of analysis can be impaired, disadvantageously.

SUMMARY OF THE INVENTION

An object of this invention is to provide, in an analytical element utilizing a reaction system in which a dye is formed by transferring a reduced type coenzyme produced under the participation of a dehydrogenase and an oxidized type coenzyme to a dye-forming precursor material through means of an electron transport agent, an analytical element that can eliminate the error originating from LDH and lactic acid present in a biological liquid sample and has been improved in the accuracy of analysis.

Summarizing the invention, this invention is an invention relating to an analytical element, and it is an analytical element for analyzing specific components in a liquid sample, comprising a light-transmissive and liquid-impermeable support having thereon a first reagent layer and a second reagent layer, and a porous spreading layer provided above said second layer, and containing an electron transport agent, a dye-forming precursor material, an oxidized type coenzyme, a buffering agent and a reagent capable of converting said oxidized type coenzyme to a reduced type coenzyme through a specific component in a liquid sample, wherein said oxidized type coenzyme is contained in said porous spreading layer, and an LHD inhibitor is contained in at least one of said second reagent layer and said porous spreading layer.

DESCRIPTION OF PREFERRED EMBODIMENTS OF THE INVENTION

This invention will be described below specifically.

The electron transport agent according to this invention is reduced in the presence of a reduced type coenzyme produced by the reaction of at least one of reagents according to this invention with an oxidized type coenzyme, through a specific component in a biological liquid sample, and the electron transport agent thus reduced further reduces a dye-forming precursor material to form a dye showing absorption at a visible region.

The specific component in a liquid sample that can be assayed in this invention may include, for example, glutamate-oxaloacetate transaminase (GOT), glutamate-pyruvate transaminase (GPT), amylase (AMY), creatine phosphokinase (CPK), and triglyceride (TG).

The reagents according to this invention may include an enzyme and, when necessary, a substrate.

These reagents can be suitably selected depending on the specific components present in the biological liquid sample to be assayed, and include, for example, aspartic acid, α-ketoglutaric acid and glutamate dehydrogenase (GlDH) in the case when assaying GOT; alanine, α-ketoglutaric acid and glutamate dehydrogenase (GlDH) in the case of GPT; maltopentose, orthophosphoric acid, β-phosphoglucomutase (β-PGM), glucose oxidase (GOD) and maltose phosphorylase (MP) in the case of AMY; creatine, adenosine triphosphate (ATP), hexokinase (HK) and glucose-6-phosphate dehydrogenase (G-6-PDH) in the case of CPK; and lipoprotein lipase (LPL), glycerokinase (GK), glycerophosphate dehydrogenase (GPDH) and adenosine triphosphate (ATP), or LPL and glycerol dehydrogenase (GDH), in the case of TG.

The oxidized type coenzyme according to this invention refers to NAD+ and NADP+. The reduced type coenzyme refers to the reduced type of the above oxidized type coenzyme. The reduced type of NAD+ is NADH, and that of NADP+ is NADPH. In this invention, NAD+ is particularly preferably used, which is therefore converted to NADH. NAD+ can improve the sensitivity for analysis of the above specific components by incorporating it into the porous spreading layer according to this invention.

In the following, shown are reaction schemes for the production of NADH by the reaction of at least one of the reagents according to this invention with NAD+ through the specific components in a biological liquid sample according to this invention.

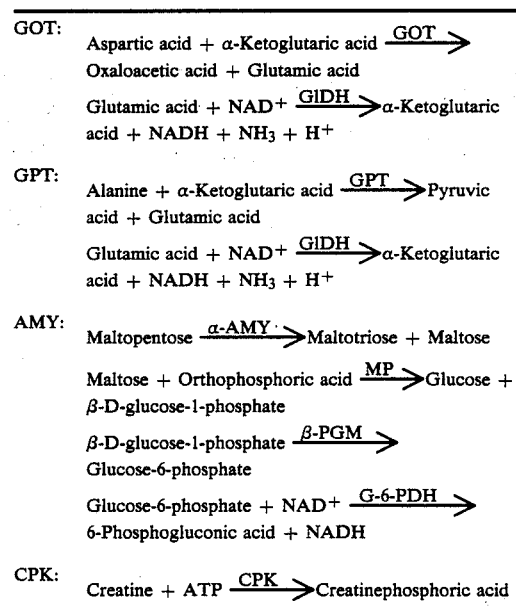

GOT:
Aspartic acid + α-Ketoglutaric acid $\xrightarrow{GOT}$ Oxaloacetic acid + Glutamic acid Glutamic acid + NAD+ $\xrightarrow{GlDH}$ α-Ketoglutaric acid + NADH + NH$_3$ + H+

GPT:
Alanine + α-Ketoglutaric acid $\xrightarrow{GPT}$ Pyruvic acid + Glutamic acid Glutamic acid + NAD+ $\xrightarrow{GlDH}$ α-Ketoglutaric acid + NADH + NH$_3$ + H+

AMY:
Maltopentose $\xrightarrow{\alpha\text{-AMY}}$ Maltotriose + Maltose

Maltose + Orthophosphoric acid $\xrightarrow{MP}$ Glucose + β-D-glucose-1-phosphate β-D-glucose-1-phosphate $\xrightarrow{\beta\text{-PGM}}$ Glucose-6-phosphate Glucose-6-phosphate + NAD+ $\xrightarrow{G\text{-}6\text{-}PDH}$ 6-Phosphogluconic acid + NADH CPK:
Creatine + ATP $\xrightarrow{CPK}$ Creatinephosphoric acid +

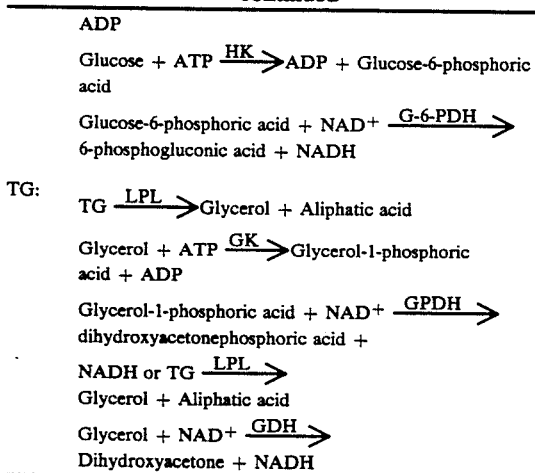

The electron transport agent used in this invention may include N-methylphenadine methosulfates (for example, N-methylphenadine methosulfate, 1-methoxy-N-methylphenadine methosulfate, etc.), Meldra's Blue, Methylene Blue, and diaphorase. Preferable electron transport agent includes N-methylphenadine methosulfate and diaphorase.

On the other hand, as the dye-forming precursor material according to this invention, tetrazolium salts are usually used. Most of the terazolium salts used in this invention may become only slightly soluble or insoluble in water after formation of a dye and can usually be used in a wet chemistry method only with difficulty, but, since the dye to be formed is diffusion-resistant, can be preferably used in view of its ability to prevent undesired ringing and improve the determinativeness of measurement.

The above tetrazolium salts regarded as being useful in this invention may include, for example, 3,3'-(3,3'-dimethoxy-4,4'-biphenylene)-bis[2-(p-nitrophenyl)-5-phenyltetrazolium chloride], 3,3'-(3,3'-dimethoxy-4,4'-biphenylene)-bis[2,5-diphenyltetrazolium chloride], 3-(4',5'-dimethyl-2-thiazolyl)-2,4-diphenyltetrazolium bromide], 3-(p-iodophenyl)-2-(p-nitrophenyl)-5-phenyltetrazolium chloride, 2,2',5,5'-tetra-(p-nitrophenyl)-3,3'-(3,3'-dimethoxy-4,4'-biphenylene)ditetrazolium chloride, 2,3,5-triphenyltetrazolium chloride, 3,3'-(3,3'-dimethoxy-4,4'-biphenylene)-bis[2,5-bis(p-nitrophenyl)-tetrazolium chloride], and 3,3'-(4,4'-biphenylene)-bis[2,5-diphenyltetrazolium chloride].

Of the above tetrazolium salts, preferably used are 3,3'-(3,3'-dimethoxy-4,4'-biphenylene)-bis[2-(p-nitrophenyl)-5-phenyltetrazolium chloride] and 3,3'-(4,4'-biphenylene)-bis[2,5-diphenyltetrazolium chloride], and these are preferably contained in the first reagent layer according to this invention.

The buffering agent used in this invention can be suitably selected depending on an optimum pH in the above reaction. For example, preferably used are tris buffering agents [those known as combinations of tris(-hydroxymethyl)aminomethane with tris(hydroxymethyl)aminomethane hydrochloride], buffers known as Good's buffering agents, carbonate buffering agents, etc.

The above buffering agent is contained preferably in a layer other than the layer containing the above dye-forming precursor material. Needless to say, laminations are formed in the state that the buffering agent and the dye-forming precursor material are not mixed at the time of production and at the time of the application of a sample. For this reason, the above buffering agents is preferably dispersed in a binder, and is preferably contained in the second reagent layer according to this invention.

The LDH inhibitor according to this invention refers to a substance capable of inhibiting the activity of LDH, and, as this LDH inhibitor, there can be used oxalic acid and a salt thereof, pyruvic acid and a salt thereof, a malonic acid and a salt thereof, oxamic acid and a salt thereof, tartronic acid and a salt thereof, ethylenediaminetetraacetic acid and a salt thereof, iodoacetamide, 2,4-dinitrofluorobenzene, mercuric (II) p-chlorobenzoate, an iodide, a silver salt, and a mercuric salt. Preferable LDH inhibitor may include oxalic acid and a salt thereof, pyruvic acid and a salt thereof, oxamic acid and a salt thereof, tartronic acid and a salt thereof, and iodoacetamide.

The above LDH inhibitor may be contained in at least one of the second reagent layer and the porous spreading layer of this invention, whereby the effect of this invention can be made particularly great.

Important are the properties of the binders which constitute the first reagent layer and the second reagent layer according to this invention. The binder for the second reagent layer is contained preferably by using a solvent showing insolubility to the binder in the first reagent layer to form the lamination. In other words, preferable combination of the binders is such that a solvent for the binder in the second reagent layer does not dissolve the binder in the first reagent layer. For example, preferable combination of the binder is such that the binder for the first reagent layer is a water soluble polymer and the binder for the second reagent layer is a hydrophilic polymer simultaneously having solubility in an organic solvent.

The binder for the formation of the first reagent layer according to this invention may include gelatin, gelatin derivatives such as phthalated gelatin, water-soluble cellulose derivatives such as hydroxyethyl cellulose and sodium carboxymethylcellulose, polyvinyl alcohols, polyacrylamides, polymethacrylamides, poly(mono- or dialkyl substituted) acrylamides, poly(mono- or dialkyl substituted) methacrylamides, and water-soluble copolymers of these. Preferably used are gelatin and derivatives thereof.

The binder for the formation of the second reagent layer of this invention may include poly(N-vinylpyrrolidone), poly(N-vinylimidazole), poly(N-vinyltriazole), and derivatives of these or copolymers of these, cellulose derivatives such as ethyl cellulose and methyl cellulose, copolymers disclosed in Japanese Unexamined Patent Publication No. 262660/1986. These copolymers are chiefly macromolecules which are soluble in alcohols such as ethanol, propanol and butanol, and also hydrophilic. Preferably used are the copolymers disclosed in the Japanese Unexamined Patent Publication No. 262660/1986.

The electron transfer agent and other various reagents according to this invention may be contained in any of the first reagent layer, the second reagent layer and the porous spreading layer.

The electron transport agent used in this invention may be contained in the analytical element in an amount that may vary depending on the amount of the above-mentioned specific components to be assayed, and in an amount of usually 1 mg/m$^2$ to 1 g/m$^2$, preferably 10 to 500 mg/m$^2$, except the case when using diaphorase.

When diaphorase is used as the electron transport agent, it is contained in an amount that varies not only depending on the amount of the above specific components but also depending on the origin of diaphorase and the manner by which the activity values are measured. It may be contained in an amount of usually 100 U/m$^2$ to 100,000 U/m$^2$, preferably 500 to 50,000 U/m$^2$.

Also, the color forming precursor material according to this invention may be contained in the analytical element of this invention in an amount of usually 10 mg/m$^2$ to 10 g/m$^2$, preferably 50 mg/m$^2$ to 3 g/m$^2$. Further, the oxidized type coenzyme according to this invention may be contained in the analytical element of this invention in an amount of usually 10 mg/m$^2$ to 50 g/m$^2$, preferably 50 mg/m$^2$ to 10 g/m$^2$.

The LDH inhibitor according to this invention may be contained in the analytical element of this invention in an amount of usually 5 mg/m$^2$ to 50 g/m$^2$, preferably 30 mg/m$^2$ to 10 g/m$^2$.

The above described liquid-impermeable and light-transmissive support according to this invention (hereinafter simply called "the support of this invention") may be any kind of supports so far as they are liquid-impermeable and light-transmissive, and suited for this use purpose are, for example, various polymeric materials such as cellulose acetate, polyethylene terephthalate, polycarbonate and polystyrene. Besides, not only such polymeric materials, it is also possible to use inorganic materials such as glass. The support of this invention may have a thickness freely determined, but preferably a thickness of 50 to 250 μm. One side face corresponding to an observation side of the support of this invention can be worked as desired according to what the analytical element is used for. When necessary, a light-transmissive subbing layer can be also provided on the side face of the support on which the reagent layers are laminated, to improve the adhesion between the reagent layer and the support.

The porous spreading layer according to this invention has a function (i) to distribute a prescribed volume of a liquid sample to a reagent layer in a uniform manner per unit area. Moreover, it should preferably has the function(s) disclosed in U.S. Pat. No. 3,992,158, which is/are a function (ii) to remove substances or factors which may inhibit the analytical reaction in a liquid sample, and/or a function (iii) to effect a background action, thereby the measuring light which transmits the support is reflected when a spectral photometric analysis is carried out. Accordingly, the porous spreading layer according to this invention can be any of a layer having only the function (i) and a layer having the function(s) (ii) and/or (iii) in addition to the function (i), or, alternatively, it is possible to use different layers for each function, wherein a plurality of the functions including the function (i) has been appropriately separated. It is also possible to use, among the functions (i), (ii) and (iii), a layer having certain two functions in combination with a layer having the remaining one function. For example, there may be included a spreading layer made of a non-fibrous porous medium called a blush polymer comprising titanium dioxide and cellulose diacetate, as disclosed in U.S. Pat. No. 3,992,158 mentioned above; a spreading layer comprising woven fabric having been made hydrophilic, as disclosed in U.S. Pat. No. 4,292,272; spreading layers having fibrous structure, as disclosed in U.S. Pat. Nos. 4,594,224, and 4,427,632, or a filter paper; and a spreading layer having particulate link structure, as disclosed in U.S. Pat. No. 4,430,436. In particular, the above spreading layers having fibrous structure and the spreading layer having particulate link structure are particularly useful as materials capable of quickly transporting blood cell portions also. The film thickness of the spreading layer in the analytical element of this invention should be determined depending on the porosity of the layer, but it may preferably be about 100 to 500 μm, more preferably about 150 to 350 μm. Also, the porosity may preferably be about 20 to 85%.

As other auxiliary additives, various additives such as preservatives and surface active agents can be optionally added.

In particular, the surface active agent can be effectively used for controlling the penetration rate when a liquid sample is applied to the analytical element of this invention.

As the surface active agents, although they can be used whether they are ionic (anionic or cationic) or nonionic, nonionic surface active agents can be used effectively. Examples of the nonionic surface active agents may include polyalkylene glycol derivatives of alkyl substituted phenols such as 2,5-di-t-butylphenoxy polyethylene glycol, p-octylphenoxy polyethylene glycol and p-isononylphenoxy polyethylene glycol; polyalkylene glycol esters of higher aliphatic acids; etc. These surface active agents have an effect to control the rate of impregnation of a liquid sample to a reagent layer or layers, and simultaneously to suppress the occurrence of undesirable "chromatography phenomenon".

The above surface active agent can be used in an amount selected from a wide range, and may be used in an amount of 25 to 0.005% by weight, preferably 15 to 0.05% by weight, based on the amount of a coating solution.

The analytical element of this invention can be made to have the desired structure fitted for the purpose of this invention, by optionally using in combination, for example, a reflection layer and a subbing layer as disclosed in U.S. Pat. No. 3,992,158, a radiation blocking layer as disclosed in U.S. Pat. No. 4,042,335, a barrier layer as disclosed in U.S. Pat. No. 4,066,403, a migration blocking layer as disclosed in U.S. Pat. No. 4,166,093, a scavenger layer as disclosed in U.S. Pat. No. 4,258,001, and a rupturable pod-like member as disclosed in U.S. Pat. No. 4,110,079.

These various layers in the analytical element can be successively laminated on the support according to this invention in the desired constitution to provide layers having desired thickness, by suitably selecting and using a slide hopper coating method, an extrusion coating method, a dip coating method, etc. which have been conventionally known in the technical field of photography.

By use of the analytical element of this invention, quantity of specific components in a liquid sample can be measured according to an initial velocity method or a reaction end point method by using a reflection spectrophotometry from the side of the support of this invention. Measured values thus obtained may be adapted to analytical curves prepared in advance, to determine the quantity of specific components.

The quantity of the liquid sample to be applied to the analytical element of this invention can be selected as desired, but it is preferably about 5 μl to about 50 μl, more preferably 5 μl to 20 μl. In ordinary cases, it is preferred to apply 10 μl of the liquid sample.

The analytical element of this invention can be used without any inconveniences for analyses of any of whole blood, serum and plasma. It can be also used without any inconveniences, for analyses of other body fluids such as urine, lymph, cerebrospinal fluid, etc. When the whole blood is used, the above radiation blocking layer or other reflection layer may be provided as necessary in order to prevent the radiation for detection from being blocked by blood cells.

This invention will be described below in greater detail by making reference to Examples, but by no means limited to these Examples.

EXAMPLE 1

(Analytical Elements for GOT)

The first reagent layers comprising the following formulation were provided on transparent polyethylene terephthalate supports of 180 μm thick, provided with a subbing layer.

| First reagent layer (R-1-1): | |
| --- | --- |
| Gelatin | 21.0 g/m$^2$ |
| Glutamate dehydrogenase | 42,000 U/m$^2$ |
| Diaphorase | 2,100 U/m$^2$ |
| 3,3'-(4,4'-Biphenylene)-bis(2,5-diphenyltetrazolium chloride) | 1.0 g/m$^2$ |
| Triton X-100 (Rohm & Hass Co.) | 2.1 g/m$^2$ |
| 1,2-Bis(vinylsulfonyl)ethane | 0.15 g/m$^2$ |

On the above first reagent layers, the second reagent layers and the spreading layers shown in the following tables were successively provided to produce analytical elements-1 to 3 of this invention and a comparative analytical element-1 as shown in Table 1.

| Second reagent layer (R-2): | R-2-1 | R-2-2 |
| --- | --- | --- |
| Tris(hydroxymethyl)aminomethane (g/m$^2$) | 5.70 | 5.70 |
| Tris(hydroxymethyl)aminomethane hydrochloride (g/m$^2$) | 1.22 | 1.22 |
| Disodium oxalate (g/m$^2$) | — | 0.3 |
| Luviskol VA-28*[1] (g/m$^2$) | 2.0 | 2.0 |
| Triton X-100 (g/m$^2$) | 0.5 | 0.5 |

*[1]Trade name owned by BASF Corp.; N-vinyl pyrrolidone/vinyl acetate copolymer (molar ratio: 20:80)
*The above second layers were coated by direct dispersion using a sand grinder, with use of n-butanol as a solvent.

| Spreading layer (S): | S-1 | S-2 | S-3 | S-4 |
| --- | --- | --- | --- | --- |
| Powdery filter paper (g/m$^2$) (Toyo Roshi K. K.; 40–100 mesh) | 91 | 91 | 91 | 91 |
| Monosodium aspartate (g/m$^2$) | 4.1 | 4.1 | 4.1 | 4.1 |
| α-Ketoglutaric acid (g/m$^2$) | 0.5 | 0.5 | 0.5 | 0.5 |
| NAD$^+$ (g/m$^2$) | 5.5 | 5.5 | 5.5 | 5.5 |
| Oxalic acid.2H$_2$O (g/m$^2$) | — | 0.2 | 0.4 | — |
| Potassium oxamate (g/m$^2$) | — | — | — | 0.8 |
| Styrene/glycidyl methacrylate copolymer (weight ratio: 9:1) (g/m$^2$) | 22 | 22 | 22 | 22 |
| Triton X-100 (g/m$^2$) | 9 | 9 | 9 | 9 |

*Coated using a xylene solvent.
*Monosodium aspartate, NAD$^+$ and potassium oxamate were added separately by direct dispersion using a sand grinder, with use of xylene as a solvent.
*α-Ketoglutaric acid and oxalic acid.2H$_2$O were added after having been dissolved in methanol.

TABLE 1

| Analytical element number | 1st Reagent layer | 2nd Reagent layer | Spreading layer |
| --- | --- | --- | --- |
| Analytical element-1 of the invention | R-1-1 | R-2-1 | S-3 |
| Analytical element-2 of the invention | R-1-1 | R-2-2 | S-2 |
| Analytical element-3 of the invention | R-1-1 | R-2-1 | S-4 |
| Comparative analytical element-1 | R-1-1 | R-2-1 | S-1 |

With respect to the above analytical elements-1 to 3 of the invention and comparative analytical element-1, 10 μl each of pool serums obtained by adding 0, 10, 20 and 30 mg/dl of lithium lactate, respectively, to (i) dialyzed pool serums (GOT: 25 K-U; LDH: 250 W-U), (ii) pool serums to which GOT (Sigma Co.; porcine heart) was added (GOT: 90 K-U; LDH: 250 W-U), and (iii) pool serums obtained by adding LDH (Sigma Co.; rabbit muscle) to the above respective pool serums (i) and (ii) (GOT: 25 K-U; LDH: 730 W-U, and GOT: 90 K-U; LDH: 730 W-U) were dropwise applied on each of the spreading layers, followed by incubation at 37° C., and the reflection density at 7 minutes and 11 minutes after the dropwise application was measured using a reflection spectrophotometer through a filter of 546 nm to determine the difference between the respective reflection density, whereupon the results as shown in Table 2 were obtained.

TABLE 2

| | GOT (K—U) 25 | | | | GOT (K—U) 90 | | | |
| --- | --- | --- | --- | --- | --- | --- | --- | --- |
| | LDH (W—U) 250 | | | | LDH (W—U) 250 | | | |
| Lithium lactate (mg/dl) | 0 | 10 | 20 | 30 | 0 | 10 | 20 | 30 |
| Analytical element-1 of the invention | 0.030 | 0.030 | 0.031 | 0.032 | 0.101 | 0.102 | 0.102 | 0.103 |
| Analytical element-2 of the invention | 0.028 | 0.029 | 0.030 | 0.030 | 0.098 | 0.098 | 0.099 | 0.100 |
| Analytical element-3 of the invention | 0.029 | 0.031 | 0.031 | 0.032 | 0.097 | 0.098 | 0.100 | 0.101 |
| Comparative analytical element-1 | 0.032 | 0.042 | 0.051 | 0.060 | 0.103 | 0.111 | 0.119 | 0.127 |

| | GOT (K—U) 25 | | | | GOT (K—U) 90 | | | |
| --- | --- | --- | --- | --- | --- | --- | --- | --- |
| | LDH (W—U) 730 | | | | LDH (W—U) 730 | | | |
| Lithium lactate (mg/dl) | 0 | 10 | 20 | 30 | 0 | 10 | 20 | 30 |
| Analytical element-1 of the invention | 0.029 | 0.029 | 0.030 | 0.030 | 0.103 | 0.103 | 0.104 | 0.104 |

TABLE 2-continued

|  |  |  |  |  |  |  |  |  |
|---|---|---|---|---|---|---|---|---|
| Analytical element-2 of the invention | 0.027 | 0.028 | 0.028 | 0.029 | 0.101 | 0.102 | 0.103 | 0.103 |
| Analytical element-3 of the invention | 0.028 | 0.028 | 0.029 | 0.030 | 0.101 | 0.102 | 0.104 | 0.104 |
| Comparative analytical element-1 | 0.030 | 0.039 | 0.047 | 0.055 | 0.105 | 0.113 | 0.120 | 0.126 |

As is apparent from the results shown in Table 2, it is seen that the comparative analytical element-1 containing no LDH inhibitor is greatly subject to the influence of LDH and lactic acid, but, in contrast thereto, the analytical elements-1 to 3 of this invention containing the LDH inhibitor (oxalic acid or a salt thereof, oxamate) are little subject to the same influence to have improved in the accuracy of analysis.

EXAMPLE 2

(Analytical Elements for GPT)

The first reagent layers comprising the following formulation were provided on transparent polyethylene terephthalate supports of 180 μm thick, provided with a subbing layer.

| First reagent layer (R-1-2): | |
|---|---|
| Gelatin | 21.0 g/m$^2$ |
| Glutamate dehydrogenase | 21,000 U/m$^2$ |
| Diaphorase | 2,100 U/m$^2$ |
| 3,3'-(4,4'-Biphenylene)-bis(2,5-diphenyltetrazolium chloride) | 1.0 g/m$^2$ |
| Triton X-100 (Rohm & Hass Co.) | 2:1 g/m$^2$ |
| 1,2-Bis(vinylsulfonyl)ethane | 0.15 g/m$^2$ |

On the above first reagent layers, the second reagent layers and the spreading layers shown in the following tables were successively provided to produce analytical elements-4 to 6 of this invention and a comparative analytical element-2 as shown in Table 3.

| Second reagent layer (R-2): | R-2-3 | R-2-4 |
|---|---|---|
| Tris(hydroxymethyl)aminomethane (g/m$^2$) | 5.70 | 5.70 |
| Tris(hydroxymethyl)aminomethane hydrochloride (g/m$^2$) | 1.22 | 1.22 |
| Disodium oxalate (g/m$^2$) | — | 0.3 |
| Luviskol VA-28 (g/m$^2$) | 3.0 | 3.0 |
| Triton X-100 (g/m$^2$) | 0.5 | 0.5 |

*The above second layers were coated by direct dispersion using a sand grinder, with use of n-butanol as a solvent.

| Spreading layer (S) | S-5 | S-6 | S-7 | S-8 |
|---|---|---|---|---|
| Powdery filter paper (g/m$^2$) (Toyo Roshi K. K.; 40–100 mesh) | 91 | 91 | 91 | 91 |
| Alanine (g/m$^2$) | 2.2 | 2.2 | 2.2 | 2.2 |
| α-Ketoglutaric acid (g/m$^2$) | 0.25 | 0.25 | 0.25 | 0.25 |
| NAD$^+$ (g/m$^2$) | 5.5 | 5.5 | 5.5 | 5.5 |
| Oxalic acid.2H$_2$O (g/m$^2$) | — | 0.2 | 0.4 | — |
| Potassium oxamate (g/m$^2$) | — | — | — | 0.8 |
| Styrene/glycidyl methacrylate copolymer (weight ratio: 9:1) (g/m$^2$) | 22 | 22 | 22 | 22 |
| Triton X-100 (g/m$^2$) | 9 | 9 | 9 | 9 |

*Coated using a xylene solvent.
*Alanine, NAD$^+$ and potassium oxamate were added separately by direct dispersion using a sand grinder, with use of xylene as a solvent.
*α-Ketoglutaric acid and oxalic acid.2H$_2$O were added after having been dissolved in methanol.

TABLE 3

| Analytical element number | 1st Reagent layer | 2nd Reagent layer | Spreading layer |
|---|---|---|---|
| Analytical element-4 of the invention | R-1-2 | R-2-3 | S-7 |
| Analytical element-5 of the invention | R-1-2 | R-2-4 | S-6 |
| Analytical element-6 of the invention | R-1-2 | R-2-3 | S-8 |
| Comparative analytical element-2 | R-1-2 | R-2-3 | S-5 |

With respect to the above analytical elements-4 to 6 of the invention and comparative analytical element-2, 10 μl each of pool serums obtained by adding 0, 10, 20 and 30 mg/dl of lithium lactate, respectively, to (i) dialyzed pool serums (GPT: 20 K-U; LDH: 250 W-U), (ii) pool serums to which GPT (Sigma Co.; porcine heart) was added (GPT: 80 K-U; LDH: 250 W-U), and (iii) pool serums obtained by adding LDH (Sigma Co.; rabbit muscle) to the above respective pool serums (i) and (ii) (GPT: 20 K-U; LDH: 730 W-U, and GPT: 80 K-U; LDH: 730 W-U) were dropwise applied on each of the spreading layers, followed by incubation at 37° C., and the reflection density at 7 minutes and 11 minutes after the dropwise application was measured using a reflection spectrophotometer through a filter of 546 nm to determine the difference between the respective reflection density, whereupon the results as shown in Table 4 were obtained.

TABLE 4

| | GPT (K—U) | | | | | | | |
|---|---|---|---|---|---|---|---|---|
| | 20 | | | | 80 | | | |
| | LDH (W—U) | | | | | | | |
| | 250 | | | | 250 | | | |
| Lithium lactate (mg/dl) | 0 | 10 | 20 | 30 | 0 | 10 | 20 | 30 |
| Analytical element-4 of the invention | 0.022 | 0.023 | 0.023 | 0.024 | 0.088 | 0.089 | 0.090 | 0.090 |
| Analytical element-5 of the invention | 0.021 | 0.021 | 0.022 | 0.023 | 0.086 | 0.087 | 0.087 | 0.088 |
| Analytical element-6 of the invention | 0.020 | 0.021 | 0.022 | 0.023 | 0.084 | 0.085 | 0.086 | 0.087 |
| Comparative analytical | 0.025 | 0.036 | 0.046 | 0.055 | 0.091 | 0.100 | 0.109 | 0.117 |

TABLE 4-continued element-2

| Lithium lactate (mg/dl) | GPT (K—U) | | | | | | | |
|---|---|---|---|---|---|---|---|---|
| | 20 | | | | 80 | | | |
| | LDH (W—U) | | | | | | | |
| | 730 | | | | 730 | | | |
| | 0 | 10 | 20 | 30 | 0 | 10 | 20 | 30 |
| Analytical element-4 of the invention | 0.021 | 0.021 | 0.021 | 0.022 | 0.087 | 0.086 | 0.087 | 0.088 |
| Analytical element-5 of the invention | 0.020 | 0.021 | 0.022 | 0.022 | 0.084 | 0.085 | 0.086 | 0.086 |
| Analytical element-6 of the invention | 0.022 | 0.023 | 0.024 | 0.024 | 0.086 | 0.087 | 0.089 | 0.088 |
| Comparative analytical element-2 | 0.024 | 0.033 | 0.041 | 0.049 | 0.089 | 0.097 | 0.104 | 0.112 |

As is apparent from the results shown in Table 4, it is seen that the comparative analytical element-2 containing no LDH inhibitor is greatly subject to the influence of LDH and lactic acid, but, in contrast thereto, the analytical elements-4 to 6 of this invention containing the LDH inhibitor (oxalic acid or a salt thereof, oxamate) are little subject to the same influence to have improved in the accuracy of analysis.

EXAMPLE 3

(Analytical Elements for TG)

The first reagent layers comprising the following formulation were provided on transparent polyethylene terephthalate supports of 180 μm thick, provided with a subbing layer.

| First reagent layer (R-1-3): | |
|---|---|
| Gelatin | 21.0 g/m² |
| Glycerol dehydrogenase | 5,000 U/m² |
| Diaphorase | 2,000 U/m² |
| 3,3'-(4,4'-Biphenylene)-bis(2,5-diphenyltetrazolium chloride) | 0.8 g/m² |
| Triton X-100 | 2.1 g/m² |
| 1,2-Bis(vinylsulfonyl)ethane | 0.15 g/m² |

On the above first reagent layers, the second reagent layers and the spreading layers shown in the following tables were successively provided to produce analytical elements-7 to 9 of this invention and a comparative analytical element-3 as shown in Table 5.

| Second reagent layer (R-2): | R-2-5 | R-2-6 |
|---|---|---|
| 3-Cyclohexylaminopropane sulfonic acid (g/m²) | 61 | 61 |
| Potassium carbonate.3/2H₂O (g/m²) | 1.8 | 1.8 |
| Sodium pyruvate (g/m²) | — | 0.7 |
| Luviskol VA-28 (g/m²) | 4.5 | 4.5 |
| Triton X-100 (g/m²) | 0.5 | 0.5 |

*The above second layers were coated by direct dispersion using a sand grinder, with use of n-butanol as a solvent.

| Spreading layer (S): | S-9 | S-10 | S-11 | S-12 |
|---|---|---|---|---|
| Powdery filter paper (g/m²) (Toyo Roshi K. K.; 40-100 mesh) | 91 | 91 | 91 | 91 |
| NAD⁺ (g/m²) | 3.1 | 3.1 | 3.1 | 3.1 |
| Lipoprotein lipase (g/m²) | 4000 | 4000 | 4000 | 4000 |
| Lithium pyruvate (g/m²) | — | 0.5 | 1.0 | — |
| Oxalic acid.2H₂O (g/m²) | — | — | — | 0.4 |
| Styrene/glycidyl methacrylate copolymer (weight ratio: 9:1) (g/m²) | 22 | 22 | 22 | 22 |
| Triton X-100 (g/m²) | 9 | 9 | 9 | 9 |

*Coated using a xylene solvent.
*NAD⁺ and lithium pyruvate were added separately by direct dispersion using a sand grinder, with use of xylene as a solvent.
*Oxalic acid.2H₂O were added after having been dissolved in methanol.
*Lipoprotein lipase used was obtained by dissolving and homogeneously stirring it together with bovine serum albumin, followed by freeze-drying to prepare freeze-dried lipoprotein lipase/bovine serum albumin powder, which was then sieved through a 200 mesh screen.

TABLE 5

| Analytical element number | 1st Reagent layer | 2nd Reagent layer | Spreading layer |
|---|---|---|---|
| Analytical element-7 of the invention | R-1-3 | R-2-5 | S-11 |
| Analytical element-8 of the invention | R-1-3 | R-2-6 | S-10 |
| Analytical element-9 of the invention | R-1-3 | R-2-5 | S-12 |
| Comparative analytical element-3 | R-1-3 | R-2-5 | S-9 |

With respect to the above analytical elements-7 to 9 of the invention and comparative analytical element-3, 10 μl each of pool serums obtained by adding 0, 10, 20 and 30 mg/dl of lithium lactate, respectively, to (i) dialyzed pool serums (TG: 125 mg/dl; LDH: 250 W-U), (ii) pool serums to which LDH (Sigma Co.; rabbit muscle) was added (TG: 125 mg/dl; LDH: 730 W-U) were dropwise applied on each of the spreading layers, followed by incubation at 37° C. for 7 minutes, and the reflection density after that was measured using a reflection spectrophotometer through a filter of 546 nm to obtain the results shown in Table 6.

TABLE 6

| | TG (mg/dl) | | | | | | | |
|---|---|---|---|---|---|---|---|---|
| | 125 | | | | 125 | | | |
| | LDH (W—U) | | | | | | | |
| | 250 | | | | 730 | | | |
| Lithium lactate (mg/dl) | 0 | 10 | 20 | 30 | 0 | 10 | 20 | 30 |
| Analytical element of the invention-7 | 1.310 | 1.312 | 1.315 | 1.318 | 1.314 | 1.318 | 1.323 | 1.326 |
| Analytical element of the invention-8 | 1.322 | 1.323 | 1.329 | 1.331 | 1.325 | 1.330 | 1.334 | 1.338 |
| Analytical element of the invention-9 | 1.302 | 1.304 | 1.307 | 1.310 | 1.306 | 1.310 | 1.315 | 1.318 |
| Comparative analytical element-3 | 1.358 | 1.413 | 1.470 | 1.521 | 1.380 | 1.473 | 1.561 | 1.649 |

As is apparent from the results shown in Table 6, it is seen that the comparative analytical element-3 containing no LDH inhibitor is greatly subject to the influence of LDH and lactic acid, but, in contrast thereto, the analytical elements-7 to 9 of this invention containing the LDH inhibitor (lithium pyruvate, oxalic acid) are little subject to the same influence to have improved in the accuracy of analysis.

Similar to the above, with respect to the analytical elements-7 to 9 of the invention and the comparative analytical element-3, 100, 200 and 300 mg/dl of triglyceride standard serums prepared using lipid serum-I and II (produced by Eiken Kagaku K.K.) were dropwise applied on the spreading layers in amount of 10 μl, followed by incubation at 37° C. for 7 minutes, and the reflection density after that was measured using a reflection spectrophotometer through a filter of 546 nm. As a result, there was seen no difference in identification ability between these analytical elements.

As described in detail in the foregoing, the analytical element of this invention can exhibit remarkable effects in that it has been made possible to carry out precise analysis without influence of LDH and lactic acid.

We claim:

1. An analytical element for analyzing a specific component selected from the group consisting of glutamate-oxaloacetate transaminase (GOT), glutamate-pyruvate transaminase (GPT), creatine phosphokinase (CPK) and triglyceride (TG), in a liquid sample, comprising a light-transmissive and liquid-impermeable support having thereon successively a first reagent layer and a second reagent layer, and a porous spreading layer provided above said second reagent layer, and containing an electron transport agent, a dye-forming precursor material, an oxidized type coenzyme, a buffering agent and at least one reagent capable of converting said oxidized type coenzyme to a reduced type coenzyme through a specific component in a liquid sample, wherein said oxidized type coenzyme is contained in said porous spreading layer, and a lactate dehydrogenase inhibitor is contained in said porous spreading layer.

2. The analytical element according to claim 1, wherein said dye-forming precursor material is contained in the first reagent layer, and said buffering agent is contained in the second reagent layer.

3. The analytical element according to claim 1, wherein said oxidized type coenzyme is an oxidized type nicotinamide adenine dinucleotide.

4. The analytical element according to claim 1, wherein said lactate dehydrogenase inhibitor is selected from the group consisting of oxalic acid and a salt thereof, pyruvic acid and a salt thereof, a malonic acid and a salt thereof, oxamic acid and a salt thereof, tartronic acid and a salt thereof, ethylenediaminetetraacetic acid and a salt thereof, iodoacetamide, 2,4-dinitrofluorobenzene, mercuric (II) p-chlorobenzoate, an iodide, a silver salt, and a mercuric salt.

5. The analytical element according to claim 1, wherein said electron transport agent is N-methylphenadine methosulfate, 1-methoxy-N-methylphenadine methosulfate, Meldra's Blue, Methylene Blue or diaphorase.

6. The analytical element according to claim 1, wherein a binder which constitutes said first reagent layer is a water soluble polymer and a binder which constitutes said second reagent layer is a hydrophilic polymer simultaneously having solubility in an organic solvent.

7. The analytical element according to claim 1, wherein said electron transport agent is contained in said analytical element in an amount of 1 mg/m$^2$ to 1 g/m$^2$, except for the case where diaphorase is used, and when diaphorase is used as the electron transport agent, it is contained in an amount of 100 U/m$^2$ to 100,000 U/m$^2$.

8. The analytical element according to claim 1, wherein said color forming precursor material is contained in said analytical element in an amount of 10 mg/m$^2$ to 10 g/m$^2$.

9. The analytical element according to claim 1, wherein said oxidized type coenzyme is contained in said analytical element in an amount of 10 mg/m$^2$ to 50 g/m$^2$.

10. The analytical element according to claim 1, wherein said LDH inhibitor is contained in said analytical element in an amount of 5 mg/m$^2$ to 50 g/m$^2$.

11. The analytical element according to claim 1, wherein the film thickness of said spreading layer is 100 to 500 μm.

12. The analytical element according to claim 1, wherein the porosity of said spreading layer is 20 to 85%.

13. The analytical element according to claim 1, wherein said dye-forming precursor material is a tetrazolium salt.

14. The analytical element according to claim 13, wherein said tetrazolium salt is 3,3'-(3,3'-dimethoxy-4,4'-biphenylene)-bis[2-(p-nitrophenyl)-5-phenyltetrazolium chloride], 3,3'-(3,3'-dimethoxy-4,4'-biphenylene)-bis[2,5-diphenyltetrazolium chloride], 3-(4',5'-dimethyl-2-thiazolyl)-2,4-diphenyltetrazolium bromide], 3-(p-iodophenyl)-2-(p-nitrophenyl)-5-phenyltetrazolium chloride, 2,2'-5,5'-tetra-(p-nitrophenyl)-3,3'-(3,3'-dimethoxy-4,4'-biphenylene)ditetrazolium chloride, 2,3,5-triphenyltetrazolium chloride, 3,3'-(3,3'- dimethoxy-4,4'-biphenylene)-bis-[2,5-bis(p-nitrophenyl)tetrazolium chloride] or 3,3'-(4,4'-biphenylene)-bis[2,5-diphenyltetrazolium chloride].

15. An analytical element for analyzing glutamate-oxaloacetate transaminase (GOT) in a liquid sample, comprising a light-transmissive and liquid-impermeable support having thereon successively a first layer and a second layer, and a porous spreading layer provided above said second layer, each of said first and second layers containing a reactant which is separately selected from the group consisting of an electron transport agent, a dye-forming precursor material, a buffering agent, aspartic acid, α-ketoglutaric acid and glutamate dehydrogenase (GlDH), with the totality of said reactants being present in said first, second and porous spreading layers and wherein said porous spreading layer further contains an oxidized type coenzyme and oxalic acid or a salt thereof as a lactate dehydrogenase inhibitor.

16. An analytical element for analyzing glutamatepyruvate transaminase (GPT) in a liquid sample, comprising a light-transmissive and liquid-impermeable support having thereon successively a first layer and a second layer, and a porous spreading layer provided above said second layer, each of said first and second layers containing a reactant which is separately selected from the group consisting of an electron transport agent, a dye-forming precursor material, a buffering agent, alanine, α-ketoglutaric acid and glutamate dehydrogenase (GlDH), with the totality of said reactants being present in said first, second and porous spreading layers and wherein said porous spreading layer further contains an oxidized type co-enzyme and oxalic acid or a salt thereof as a lactate dehydrogenase inhibitor.

17. An analytical element for analyzing creatine phosphokinase (CPK) in a liquid sample, comprising a light-transmissive and liquid-impermeable support having thereon successively a first layer and a second layer, and a porous spreading layer provided above said second layer, each of said first and second layers containing a reactant which is separately selected from the group consisting of an electron transport agent, a dye-forming precursor material, a buffering agent, creatine, adenosine triphosphate (ATP), hexokinase (HK) and glucose-6-phosphate dehydrogenase (G-6-PDH), with the totality of said reactants being present in said first, second and porous spreading layers and wherein said porous spreading layer further contains an oxidized type coenzyme and oxalic acid or a salt thereof, pyruvic acid or a salt thereof is contained in said porous spreading layer as a lactate dehydrogenase inhibitor.

18. An analytical element for analyzing triglyceride (TG) in a liquid sample, a light-transmissive and liquid-impermeable support having thereon successively a first layer and a second layer, and a porous spreading layer provided above said second layer, each of said first and second layers containing a reactant which is separately selected from the group consisting of an electron transport agent, a dye-forming precursor material, a buffering agent, lipoprotein lipase (LPL), glycerokinase (GK), adenosine triphosphate (ATP) and glycerophosphate dehydrogenase (GPDH), and a combination of lipoprotein lipase (LPL) and glycerol dehydrogenase (GDH), with the totality of said reactants being present in said first, second and porous spreading layers and wherein said porous spreading layer further contains an oxidized type coenzyme and oxalic acid or a salt thereof, pyruvic acid or a salt thereof is contained in said porous spreading layer as a lactate dehydrogenase inhibitor.

* * * * *